United States Patent

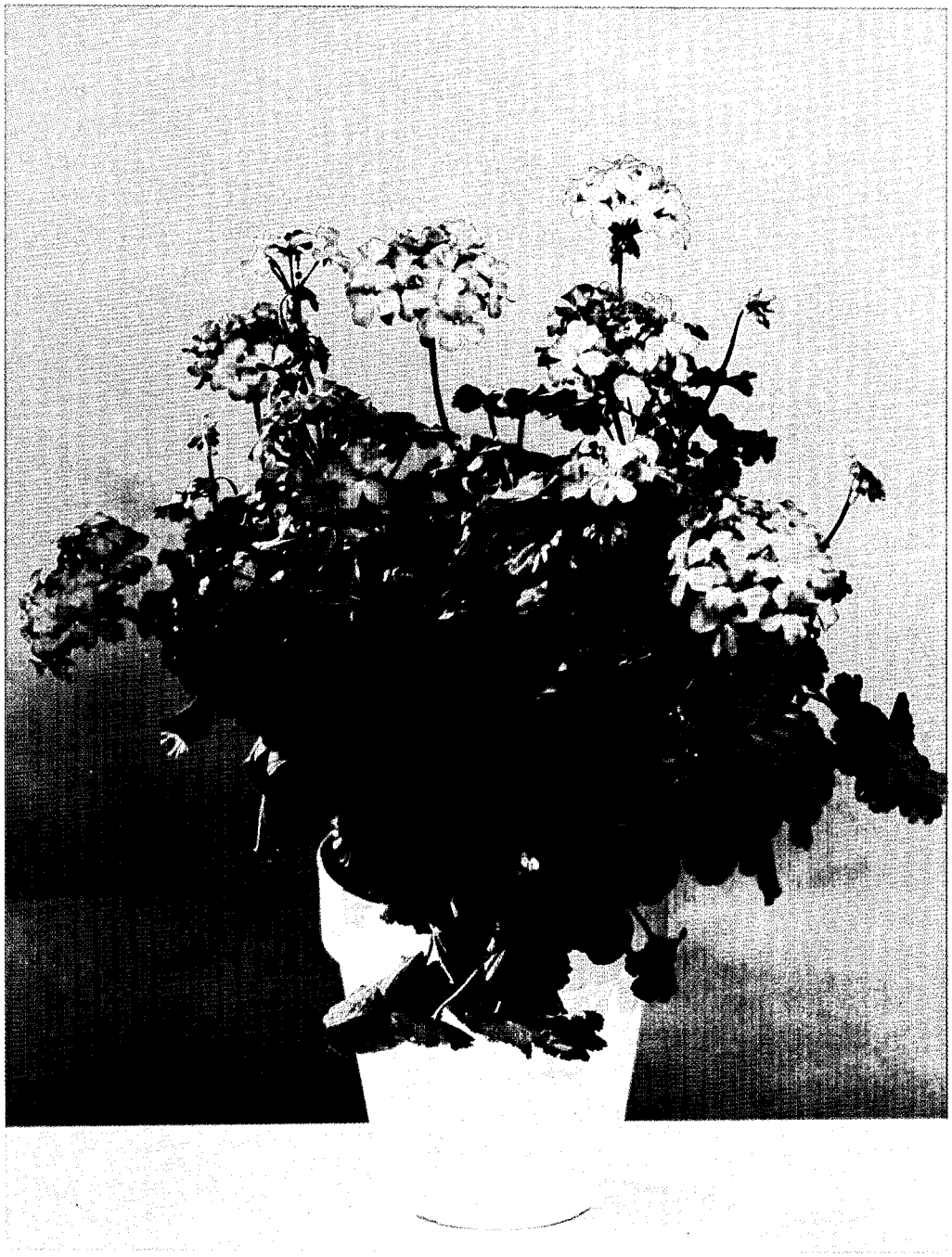

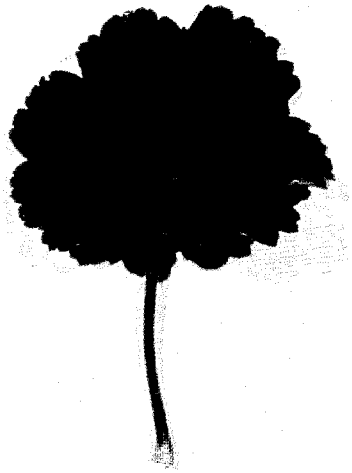
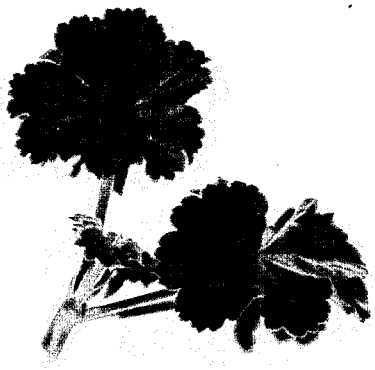
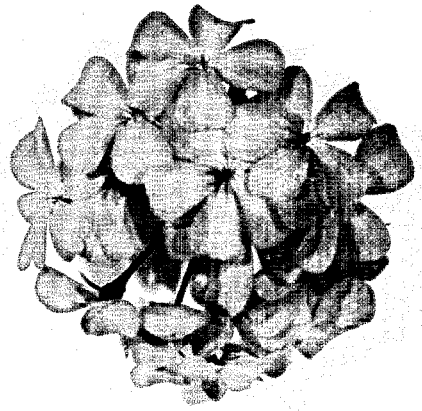
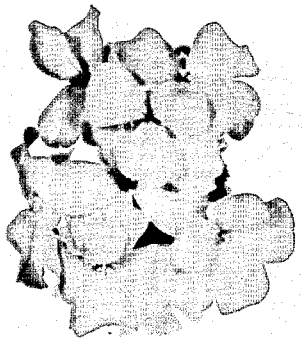

Plant Pat. 3,943

Patented Aug. 24, 1976

3,943

GERANIUM PLANT

William E. Duffett, Akron, Ohio, and Walter W. Knicely, Inwood, W. Va., assignors to Yoder Brothers, Inc., Barberton, Ohio

Filed June 20, 1975, Ser. No. 588,842

Int. Cl.[2] A01H 5/00

U.S. Cl. Plt.—68 1 Claim

The present invention comprises a new and distinct cultivar, a hybrid of the genus Pelargonium, L'Her., hereinafter referred to by the cultivar name Spry Cherub (#6891500B).

Spry Cherub was originated from a cross made under the supervision of William E. Duffett and Walter W. Knicely in a controlled breeding program in Barberton, Ohio in the year 1967.

The female, or seed parent, was #65915001 (unnamed seedling), a semi-double of scarlet red color originated by the present inventors from a cross between #62002003 (unnamed seedling) and #716 (unnamed seedling). Both parents are products of the breeding program of the present inventors.

The male, or pollen parent, was also #65915001.

Spry Cherub was discovered and selected as a flowering seedling within the progeny of the stated cross by William E. Duffett and Walter W. Knicely on Sept. 4, 1969 in an outdoor field environment in Barberton, Ohio.

Spry Cherub is a product of a planned breeding program which had the objective of creating durable, disease tolerant geraniums that would fulfill in part or in whole the need for a geranium with compact and spreading growth habit, vibrant flower color, fast spring pot response period, and prolific flowering traits under outdoor summer conditions in Ohio.

The first act of asexual reproduction of Spry Cherub was accomplished when vegetative cuttings were taken from the initial selection in September 1969, in Barberton, Ohio, by a technician under formulations established and supervised by William E. Duffett and Walter W. Knicely.

Continued asexual reproduction by vegetative cuttings for evaluative tests in flowering and stock programs in conjunction with horticultural certification initiated Sept. 22, 1970 by William E. Duffett and Walter W. Knicely have demonstrated that the combination of characteristics as herein disclosed for Spry Cherub are firmly fixed and are retained through successive generations of asexual reproduction.

The following descriptive observations, measurements, and comparisons were derived from plants grown both in a greenhouse and under outdoor field conditions. The greenhouse-grown, spring flowering containerized plants were planted in an outdoor field in late May, early June and observed during the summer and fall months. The environmental conditions under which the observed plants were grown are generally described in Local Climatological Data, Annual Summary With Comparative Data, Akron, Ohio, U.S. Department of Commerce, National Oceanic and Atmospheric Administration, Data Service, Washington, D.C. 1970, 1971, 1972, 1973, 1974. General cultural practices utilized closely approximate those generally used in commercial practice and are described in Chart A attached at the end of the present specification.

The following traits have been repeatedly observed and are determined to be basic characteristics of Spry Cherub which in combination distinguish this geranium as a new and distinct cultivar.

(1) Scarlet red flower color devoid of blue and orange tones.

(2) Compact, spreading growth habit.

(3) Prolific flowering traits under Ohio outdoor summer conditions.

(4) Durable flower and foliage under Ohio outdoor summer conditions.

(5) Fast spring pot flowering response.

The accompanying color photographic drawings show typical flower and foliage characteristics of Spry Cherub. Sheet 1 illustrates Spry Cherub in bloom, and Sheet 2 comprise a photograph showing the development of the inflorescence and the foliage of Spry Cherub. It is noted that difficulty was encountered in obtaining photographs accurately representing the true colors of Spry Cherub. The actual flower color of Spry Cherub is more intense and vibrant than represented, and the true foliage color is shown only in Sheet 2. The color readings are, however, correct.

The phenotype of Spry Cherub may vary significantly with variations in environment such as temperature, light intensity, and daylength. The genotype of Spry Cherub was not observed under all possible environments.

Of the many commercial cultivars known to the present inventors, the cultivars most similar to Spry Cherub are Irene (unpatented) and Sincerity (unpatented). Reference is made to attached Chart B which compares certain characteristics of Spry Cherub and the noted cultivars. General comparisons are as follows:

(1) In comparison to Irene, Spry Cherub has red flower color devoid of blue tones, shorter height, and better flower and foliage durability under outdoor summer conditions in Ohio. The semi-spreading growth habit, the spring flowering response period and the outdoor flower production of Spry Cherub are similar to those of Irene.

(2) In comparison to Sincerity, Spry Cherub has red flower color devoid of orange tones, more spreading growth habit, shorter height, shorter spring flowering response period, and more prolific outdoor flower production. The outdoor flower and foliage durability of Spry Cherub are similar to those of Sincerity.

In the following description, color references are to the Munsell Limit Color Cascade, 1972 edition. Color values were determined between 4:00 p.m. and 4:30 p.m. on July 24, 1974, under 150 foot candle light intensity at Barberton, Ohio.

BOTANICAL CLASSIFICATION

A hybrid of the genus Pelargonium L'Her., cv Spry Cherub.

1. Inflorescence

A. Umbel:

*Average diameter.*—2.7 inches.

*Average depth.*—2.2 inches.

*Peduncle.*—Ranges from 4 inches to 7 inches in length, averaging 5.3 inches.

*Pedicel.*—0.75 inch to 1 inch in length.

B. Corolla:

*Average diameter.*—1.5 inches.

*Type.*—Single; rotate.

*Color.*—Abaxial.—Between 36–12 and 38–8. Adaxial.—Between 36–11 and 38–12.

C. Bud:

*Shape.*—Conodial.

*Color.*—Abaxial: Between 36–12 and 37–12. Adaxial: Between 36–6 and 37–8.

D. Reproductive organs:

*Androecium.*—Stamen: Monodelphous; dorsifixed; pentadynamous. Pollen: Present.

*Gynoecium.*—Stigma: 5-lobed; linear. Carpel: 5 locules; pubescent.

E. Response period: Early. 80% of plants in plot had at least 1 flower open on May 30, 1974 from a direct stick dated of Apr. 3, 1974 (8 weeks).

F. Production: Good.

| | *Average number of flowers per plant* |
|---|---|
| July 15, 1974 | 1.4 |
| Aug. 1, 1974 | 2.3 |
| Aug. 15, 1974 | 2.3 |
| Sept. 1, 1974 | 3.0 |

G. Durability:

*Shatter resistance.*—Good.

*Tolerance of botrytis.*—Good.

II. Plant

A. Foliage:

*Form.*—Reni-form.

*Margin.*—Undulate; crenate.

*Color.*—Abaxial: Between 21–13 and 21–14. Adaxial: Approximately 21–15 but overlaid with grey. Durability (outdoor): Good.

B. Growth habit:

*Form.*—Semi-spreading.

*Height.*—Short, semi-dwarf.

*Internode length.*—Short.

C. Durability:

*Tolerance of botrytis.*—Good.

CHART A—ENVIRONMENTS FOR GERANIUM PERFORMANCE EVALUATION COMMONLY USED IN BARBERTON, OHIO

| | Environment | |
|---|---|---|
| | I. Greenhouse | II. Outdoor field |
| Period of year | April through May | June through September |
| Temperature (° F.) | Night: 62–65; Bright day; 72–75; Cloudy day; 68–70 | Uncontrolled dependent upon prevailing weather conditions. |
| Light | Uncontrolled dependent upon natural daylength and light intensity. Light shade compound on greenhouse class. | Uncontrolled dependent on natural daylength and light intensity. |
| Schedule and specifications | Take vegetative cutting: April 2. Cutting Specifications: 2–2.75 inches in length. Direct stick: April 3; 1 cutting per 4 inch plastic pot. Media: 1 part soil, 1 part peat, 1 part perlite. Move to 6″ x 7″ spacing: April 23. Flower date: May 28. | Plant: early June (product produced in I). Location: outdoor field. Media: well drained field soil. |

CHART B—COMPARISON OF SPRY CHERUB WITH IRENE AND SINCERITY

| Cultivar | Flower color | Growth habit | Height | Spring flowering response period | Outdoor flower production | Outdoor flower durability | Outdoor foliage durability |
|---|---|---|---|---|---|---|---|
| Spry Cherub | Scarlet red | Semi-spreading | Semi-dwarf | Early | Prolific | Good | Good. |
| Irene | Rose red | do | Medium | do | do | Poor | Poor. |
| Sincerity | Scarlet orange | Semi-upright | Tall | Late | Medium | Good | Good. |

NOTE.—Comparisons made of plants grown in a greenhouse and in an outdoor field in Barberton, Ohio, under cultural conditions as described in Chart A.

We claim:

1. A new and distinct cultivar of geranium plant characterized particularly as to uniqueness by the combined characteristics of scarlet red flower color devoid of blue and orange tones, compact, spreading growth habit, prolific flowering traits under Ohio outdoor summer conditions, durable flower and foliage under Ohio outdoor summer conditions, and fast spring pot flowering response.

No references cited.

ROBERT E. BAGWILL, Primary Examiner